(12) United States Patent
Simpson et al.

(10) Patent No.: US 8,193,406 B2
(45) Date of Patent: Jun. 5, 2012

(54) SUPER-HYDROPHOBIC BANDAGES AND METHOD OF MAKING THE SAME

(75) Inventors: John T. Simpson, Clinton, TN (US); Brian R. D'Urso, Pittsburgh, PA (US)

(73) Assignee: UT-Battelle, LLC, Oak Ridge, TN (US)

( * ) Notice: Subject to any disclaimer, the term of this patent is extended or adjusted under 35 U.S.C. 154(b) by 224 days.

(21) Appl. No.: 12/273,800

(22) Filed: Nov. 19, 2008

(65) Prior Publication Data

US 2009/0076430 A1  Mar. 19, 2009

Related U.S. Application Data

(63) Continuation-in-part of application No. 11/749,852, filed on May 17, 2007, now abandoned.

(51) Int. Cl.
*A61F 13/00* (2006.01)
*B32B 3/26* (2006.01)
(52) U.S. Cl. .............. 602/42; 428/315.5; 428/315.7; 428/316.6; 427/2.31; 977/931
(58) Field of Classification Search .............. 602/42; 428/315.5, 315.7, 316.6; 427/2.31; 977/931
See application file for complete search history.

(56) References Cited

U.S. PATENT DOCUMENTS

| | | | |
|---|---|---|---|
| 3,790,475 A | 2/1972 | Eaton | |
| 3,931,428 A | 1/1976 | Reick | |
| 6,319,868 B1 | 11/2001 | Gani et al. | |
| 2002/0142150 A1 | 10/2002 | Baumann et al. | |
| 2002/0149584 A1 | 10/2002 | Simpson et al. | |
| 2002/0150726 A1 | 10/2002 | Nun et al. | |
| 2002/0151245 A1 | 10/2002 | Hofmann et al. | |
| 2003/0013795 A1 | 1/2003 | Nun et al. | |
| 2003/0230112 A1 | 12/2003 | Ikeda et al. | |
| 2005/0176331 A1* | 8/2005 | Martin et al. | 442/396 |
| 2006/0024508 A1 | 2/2006 | D'Urso | |
| 2007/0196401 A1* | 8/2007 | Naruse et al. | 424/401 |
| 2007/0237812 A1* | 10/2007 | Patel et al. | 424/446 |
| 2009/0042469 A1 | 2/2009 | Simpson | |
| 2009/0264836 A1* | 10/2009 | Roe et al. | 604/289 |
| 2010/0286582 A1* | 11/2010 | Simpson et al. | 602/43 |

FOREIGN PATENT DOCUMENTS

| | | |
|---|---|---|
| DE | 10138036 A1 | 2/2003 |
| EP | 0985392 | 3/2000 |
| WO | 02/98562 A1 | 12/2002 |
| WO | WO 2004/048450 | 6/2004 |
| WO | 2005/091235 A1 | 9/2005 |
| WO | 2005/118501 A1 | 12/2005 |

OTHER PUBLICATIONS

Non-Final Office Action mailed Dec. 3, 2009 in parent U.S. Appl. No. 11/749,852 (19 pages).

* cited by examiner

*Primary Examiner* — Hai Vo
(74) *Attorney, Agent, or Firm* — Novak Druce + Quigg

(57) ABSTRACT

A bandage that includes a material, which can be breathable, having a first surface, and a plurality of superhydrophobic particles attached to the first surface. The plurality of superhydrophobic particles ranging in size from about 100 nanometers to about 10 micrometers. The superhydrophobic particles including a protrusive material defining a plurality of nanopores and a plurality of spaced apart nanostructures that define an external boundary of the hydrophobic particles. The nanopores providing a flow through porosity. The first surface can be rendered superhydrophobic by the attached superhydrophobic particles. The material can have a second surface opposite the first surface that is hydrophilic. The superhydrophobic particles can be adhered to the first surface by a binder. Also included is a method of making the bandages described herein.

15 Claims, 3 Drawing Sheets

SUPER-HYDROPHOBIC BANDAGES AND METHOD OF MAKING THE SAME

CROSS-REFERENCE TO RELATED APPLICATIONS

This application is a continuation-in-part of co-pending U.S. patent application Ser. No. 11/749,852, "Super-Hydrophobic Water Repellant Powder," filed May 17, 2007, the entirety of which is incorporated herein by reference.

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

The present invention relates to bandages having hydrophobic or superhydrophobic surfaces and methods of making the same.

BACKGROUND OF THE INVENTION

Bandages have long been used to support tissue and to aid wound healing. In order to allow the skin covered by a bandage to undergo transpiration it is important that the bandage is breathable. A disadvantage of current breathable bandages is that use of breathable materials results in a propensity to absorb water. This problem becomes acute when the wearer attempts to wash adjacent skin or take a shower and ends up saturating the bandage or the underlying dressing with water. Once the bandage is saturated it is necessary for the individual to re-bandage or re-dress the injury. This problem is even more pronounced with orthopedic casts, which are worn for weeks or months.

SUMMARY OF THE INVENTION

A breathable bandage having superhydrophobic particles attached to a surface thereof to prevent water from penetrating from the exterior to the interior of the bandage. The bandage can include a material having a first surface and a plurality of superhydrophobic particles attached to the first surface. The plurality of superhydrophobic particles can comprise a protrusive material defining a plurality of nanopores and a plurality of spaced apart nanostructures defining an external boundary of the hydrophobic particles. The nanopores can provide a flow through porosity. The superhydrophobic particles can range in size from about 100 nanometers to about 10 micrometers.

The plurality of attached superhydrophobic particles can render the first surface of the material superhydrophobic. The material can have a second surface, opposite the first surface, that is not superhydrophobic. The material can have a second surface, opposite the first surface, that is hydrophilic.

The bandage can also include a binder adhering the plurality of superhydrophobic particles to the first surface. The plurality of superhydrophobic particles can be mechanically bound to the first surface.

The material can be breathable. The material can be selected from the group consisting of porous films, apertured films, textiles, nonwoven materials, impregnated composites thereof, and combinations thereof.

The bandage can also include a dressing or absorbent material attached to the material. The dressing or absorbent material can be attached to a side of the material opposite the first surface. The bandage can be a bandage selected from the group consisting of an adhesive bandage, a compression bandage, a wrap, gauze, medical tape, an orthopedic cast, and combinations thereof.

The invention also includes a method of making a bandage having a water repellant surface. The method can include providing a material and attaching a plurality of particles to a first surface of the material. A plurality of superhydrophobic particles can be formed from a plurality of particles. The plurality of superhydrophobic particles can include a protrusive material defining a plurality of nanopores and a plurality of spaced apart nanostructures defining an external boundary of the hydrophobic particles. The nanopores can provide a flow through porosity. The superhydrophobic particles can range in size from about 100 nanometers to about 10 micrometers.

The first surface can be hydrophobic after the method is complete. The plurality of attached superhydrophobic particles can render a first surface of the material superhydrophobic. The plurality of particles can be applied to the first surface while the first surface is adherent, e.g., tacky.

The attaching step can include forming a mixture of the plurality of particles and a solvent, and applying the mixture to the first surface. The solvent can be volatile at a temperature of the applying step, and the first surface can be soluble in the solvent. The attaching step can include forming a mixture including a plurality of particles and an adhesive, and applying the mixture to the first surface.

The step of forming the superhydrophobic particles can occur before or after the attaching step. The material can include a second surface, opposite the first surface, that is hydrophilic after the method is complete.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

The invention includes a breathable bandage having a superhydrophobic surface. The superhydrophobic surface can prevent water from penetrating through the exterior of the bandage, while allowing water vapor to escape from the skin through the bandage to the surroundings. Thus, the breathable bandage can be breathable in order to facilitate proper healing and skin conditions, while preventing water from penetrating the bandage and wetting bandage layers closer to the skin.

Figure 1:
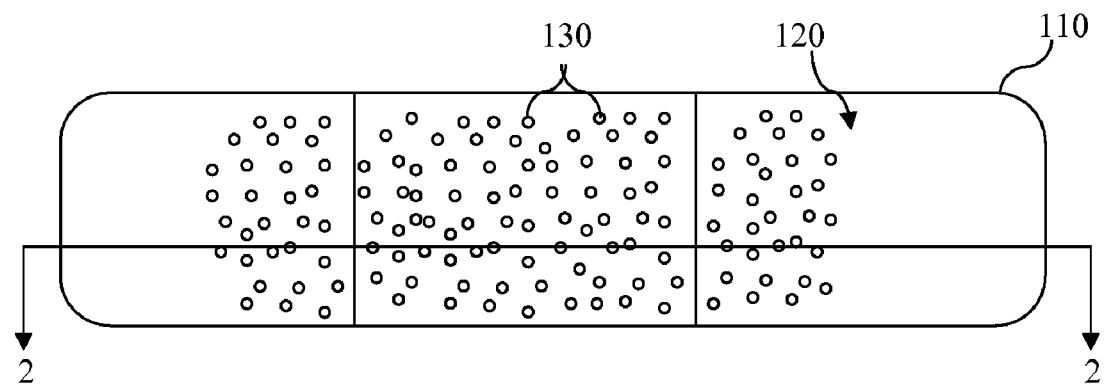
FIG. 1 is a top view of an adhesive bandage according to the invention.
Figure 2:
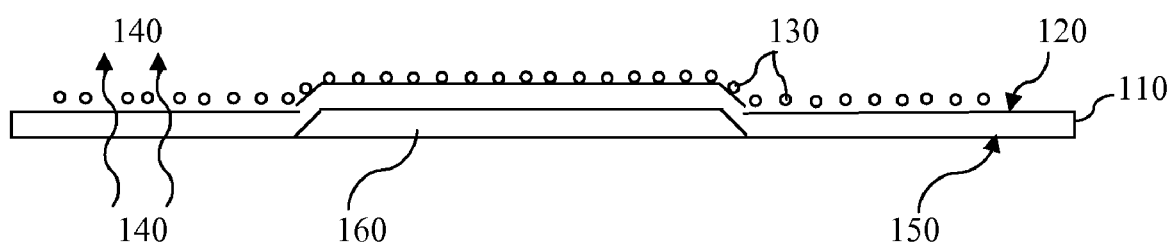
FIG. 2 is a cross-sectional view of the adhesive bandage of FIG. 1 taken along cut line 2-2.

As shown in FIGS. 1 and 2, in one embodiment, the invention is a bandage 100 that can include a material 110 having a first surface 120 and a plurality of superhydrophobic particles 130 attached to the first surface 120. The plurality of superhydrophobic particles can range in size from about 100 nanometers to about 10 micrometers. The plurality of superhydrophobic particles can have a protrusive material defining a plurality of nanopores and a plurality of spaced apart nanostructures defining an external boundary of the superhydrophobic particles. The nanopores can provide a flow through porosity. The material can be breathable.

As used herein, a material having a "flow through porosity" is porous enough that gases, such as air, can pass through the powder grain pores from one side to the other. Thus, a particle having a flow through porosity has a pore structure, whether continuous or tortuous, leading from one side of the particle to another.

Is used herein, "superhydrophobic" is used to refer to a material or surface having a contact angle with water of at least 150 degrees. For example, the superhydrophobic materials disclosed herein could have a contact angle of at least 155 degrees, at least 160 degrees, at least 165 degrees, at least 170 degrees or at least 175 degrees.

As used herein, "attached" includes physical and chemical attachment. For example, a particle can be attached to gauze where it is physically entangled in fibers forming the gauze. A particle can also be attached to a surface where the particle is bound by adhesive to the surface. In some embodiments, the adhesive can be the surface itself, such as where the particle is applied to the surface in a mixture with a volatile solvent that flash melts the surface.

The plurality of superhydrophobic particles 130 can be mechanically bound to the first surface 120. The plurality of superhydrophobic particles 130 can be chemically bound to the first surface 120. A superhydrophobic particle is chemically bound to the first surface both where the superhydrophobic particle is directly chemically bound to the first surface and where the superhydrophobic particle is chemically bound to a binder, or other intermediate layer, that is bound to the first surface. Similarly, a superhydrophobic particle is mechanically bound to the first surface both where the superhydrophobic particle is directly mechanically bound to the first surface and where the superhydrophobic particle is mechanically bound to a binder, or other intermediate layer, that is bound to the first surface.

The spaced apart nanostructures of the hydrophobic particles can define an external boundary of the superhydrophobic particles. The external boundary of the hydrophobic particles can be defined by the furthest extent of each of the plurality of spaced apart nanostructures. Thus, while the individual space apart nanostructures do not form a continuous surface, they define an external boundary or surface. As used herein, surface and external boundary are used interchangeably with respect to the superhydrophobic particles.

As used herein, "breathable" is used to refer to a material that is permeable to water vapor and gases. For example, as shown in FIG. 2, water vapor 140 can pass through a breathable bandage 100 made from a breathable substrate 110. Breathability can be measured using water vapor transmission rate (WVTR) measurements, such as that set forth in ASTM Standard E96-80. A breathable material can have a WVTR of at least about 50 g/m$^2$/day, at least about 100 g/m$^2$/day, at least about 200 g/m$^2$/day, at least about 300 g/m$^2$/day, or even at least about 500 g/m$^2$/day.

The plurality of attached superhydrophobic particles render the first surface of the material superhydrophobic. The material 110 can have a second surface 150, opposite the first surface 120, that is not superhydrophobic. The second surface 150 can even be hydrophilic. Such an embodiment, as shown in FIG. 2, can be useful where the second surface 150 is in contact with a dressing 160 and the first surface 120 forms the bandage 100 exterior, which is in contact with the environment. The second surface 150 of the material can also be hydrophobic or even rendered superhydrophobic using the techniques disclosed herein.

The bandage can also include a binder, i.e., adhesive, for adhering the plurality of superhydrophobic particles to the first surface (not shown). The binder can be any binder useful for adhesion of the particles to the target material. In some instances, the particles may be attached to the material while in a hydrophilic or hydrophobic state and converted to a superhydrophobic state only after the binder is used to adhere the particles to the first surface. This approach greatly expands the number of binders that can be useful for adhering the superhydrophobic particles to the first surface.

Exemplary binders for adhering superhydrophobic particles to the first surface include, but are not limited to, polypropylene; polystyrene; polyacrylate; cyanoacrylates; amorphous fluoropolymer, such as that sold by E. I. du Pont de Nemours and Company under the TEFLON AF® trademark; acrylic copolymer and alkyd resin mixtures, such as those sold by Rohm and Haas under the FASTRACK XSR® trademark. Exemplary binders for adhering hydrophilic or hydrophobic particles include, but are not limited to, polycyanoacrylates, polyacrylates, polysiloxanes, polyisobutylene, polyisoprene, styrenes, polyvinylpyrrolidone, polyvinyl alcohol, styrene block copolymers, block amide copolymers, and copolymers and mixtures thereof. The binder can be applied as a polymer, e.g., polypropylene, polystyrene, dissolved in a solvent. The binders can include further components, including tackifiers, plasticizers and other components typically found in binders.

One consideration for producing the claimed bandages is that the unique topography of the particles enhances the superhydrophobic nature of the particles. In order to produce the desired superhydrophobic material surface, the particle-binder mixture should be formulated to avoid coating of the spaced apart nanostructures by the binder in a manner that substantially diminishes the topography generated by the etching steps described herein. One method of achieving this objective is to dilute the mixture with an appropriate solvent, such as an organic solvent. The organic solvent can be, but is not necessarily, volatile at room temperature, e.g., 22-25° C. Organic solvents that may be useful include, but are not limited to, acetone, methyl ethyl ketone, ethyl acetate, toluene, methyl isobutyl ketone, tetrahydrofuran, cyclohexanone, methanol, n-propanol, n-hexane, and perfluorinated liquids. Exemplary perfluorinated liquids can be obtained from 3M Company under the FLUORINERT® trademark.

It can be desirable for the distribution of the superhydrophobic particles in the mixtures described herein to be as homogeneous as possible. Homogeneity of the superhydrophobic particles can be enhanced by use of a dispersant to prevent the superhydrophobic particles from agglomerating in the mixture. Exemplary dispersants include hexanes, ethanol, acetone, isopropyl alcohol, and FLUORINERT®, such as FC-40 and FC-75. In addition, a mechanical means, such as sonication, can also be used to induce dispersion of these superhydrophobic particle comprising solutions and mixtures.

The bandage substrate can be selected from the group consisting of porous or perforated films, textiles, nonwoven materials, impregnated composites thereof, and combinations thereof. The bandage substrate can be an elastic material, such as a woven material containing elastomeric fibers, or a laminate of one or more bandage layers with one or more elastomeric layers. Impregnated composites can include orthopedic casts and similar bandages. As used herein, the term bandage is intended to include wraps that are applied over existing bandages in order to prevent saturation of the underlying bandage.

As shown in FIG. 2, the bandage 100 can include a dressing 160, such as an absorbent material, attached to the material 110. The dressing 160 can be adjacent to a second surface 150 opposite the first surface 120. The bandage can be any bandage including, but not limited to, an adhesive bandage, a compression bandage, a wrap, gauze, medical tape, an orthopedic cast, and combinations thereof.

In another embodiment, the invention includes a method of making a bandage having a water repellant surface. The method can include providing a material, attaching a plurality of particles to a first surface of the material, and forming a plurality of superhydrophobic particles from a plurality of particles. The plurality of superhydrophobic particles can include a protrusive material defining a plurality of nanopores and a plurality of spaced apart nanostructures defining an external boundary of the superhydrophobic particles. The nanopores can provide a flow through porosity and the superhydrophobic particles can range in size from about 100 nanometers to about 10 micrometers. The complete method can produce a first surface that is hydrophobic after the method is complete. The complete method can produce a first surface that is superhydrophobic after the method is complete. A second surface opposite the first surface can be hydrophilic after the method is complete.

The attaching step can include forming a mixture comprising the plurality of particles and a solvent, and applying the mixture to the first surface of the material. The amount of DE particles in the mixtures described herein can generally range from 0.2 wt-% to 10 wt-%, or between 0.5 wt-% to 8 wt-%.

Figure 3:
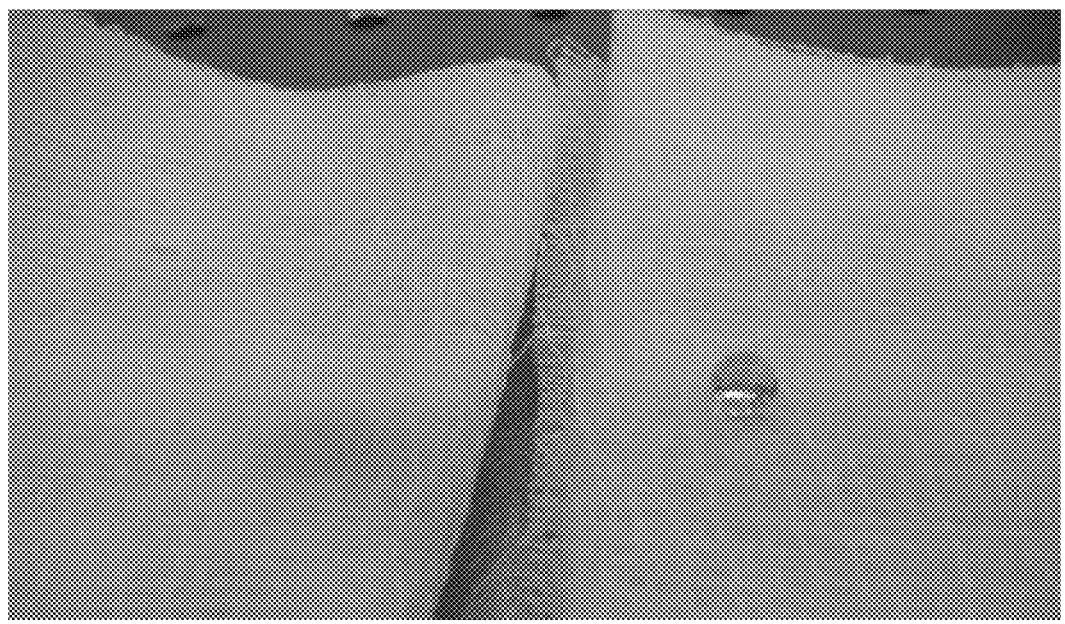
FIG. 3 is an optical picture comparing a drop of water applied to gauze (left) and a drop of water applied to a superhydrophobic gauze surface (right) produced according to an embodiment of the invention.

An exemplary mixture can be a solution containing 1 wt-% superhydrophobic particles in a solvent, e.g., ethanol. The ethanol mixture can be applied to a gauze. Once the ethanol evaporates, the superhydrophobic particles can become entangled in the gauze and produce a superhydrophobic gauze surface. FIG. 3 shows a comparison of a gauze treated in this manner with superhydrophobic particles (right) compared with a gauze that is identical except that it was not treated with the superhydrophobic particles (left). Similarly, a solution of superhydrophobic particles and acetone could be applied to a bandage material, such as an orthopedic cast, and the acetone allowed to evaporate.

The attaching step can be a "flash melting" step where the solvent is volatile at the applying step temperature and the first surface is soluble in the solvent. In such an embodiment, the first surface can be a polymer that is soluble in the solvent. When the mixture is applied, the first surface can begin to solubilize into the mixture as the solvent is volatilizing into the atmosphere. This will cause the solubilized portion of the first surface to precipitate over a portion of the superhydrophobic particles, thereby attaching the particles to the first surface.

Examples of flash melting include a solution of acetone and 1 wt-% superhydrophobic particles applied to a polypropylene bandage material. Another example includes applying to a polyvinylchloride containing material a solution of 1 wt-% superhydrophobic particles in tetrahydrofuran, methyl ethyl ketone and, optionally, cyclohexanone. A mixture of tetrahydrofuran, methyl ethyl ketone and, optionally, cyclohexanone is sold as PVC Primer and can be purchased from numerous companies, including Cantex, Inc.

In another embodiment, the attaching step can include forming a mixture comprising the plurality of particles and an adhesive, and applying the adhesive mixture to the first surface. The adhesive can be applied as a polymer, e.g., polypropylene, polystyrene, dissolved in a solvent. As noted above, a solvent, a dispersant, a diluent, or any combination can be added to the particulate-adhesive mixture in order to produce the desired superhydrophobic surface.

The adhesive mixture can include 1 wt-% superhydrophobic particles and 0.1 wt-% cyanoacrylate monomer in acetone. Another adhesive mixture can include 1 wt-% superhydrophobic particles and 0.1 wt-% polypropylene in acetone. Yet another adhesive mixture can include 1 wt-% superhydrophobic particles and 0.1 wt-% amorphous fluoropolymer, such as TEFLON AF® sold by DuPont, in a perfluorinated solvent, such as FLUORINERT® available from 3M Corp. Another adhesive mixture is 1 wt-% superhydrophobic particles and 0.1 wt-% of an acrylic copolymer and alkyd resin mixture, such as that sold by Rohm and Haas under the FASTRACK XSR® trademark, in acetone.

The mixtures described above can be applied to the material using any appropriate techniques including, but not limited to, dipping, painting, printing, and spraying. For example, the mixture can be printed onto the material using a gravure roll or an inkjet-type print head.

In another embodiment, the attaching step can include applying the plurality of particles to the first surface while the first surface is adherent. For example, the superhydrophobic particles can be sprinkled onto the surface of an orthopedic cast while the exterior of the cast is still drying. Another example, would be to apply superhydrophobic particles to the surface of an extruded material shortly after extrusion from the die tip and prior to quenching. In both cases, the superhydrophobic particles are applied to the first surface while the material is still adherent, thereby producing a bandage with superhydrophobic particles directly adhered to the surface.

The forming step can occur either before or after the attaching step. This provides flexibility regarding any number of features of the method. For example, forming the superhydrophobic particles after the attaching step allows use of a broad range of aqueous solvents for the attaching step. A benefit of forming the superhydrophobic particles prior to attachment is that the other elements of the bandage are not exposed to the moieties used to add the hydrophobic functionality to the superhydrophobic particles.

The superhydrophobic particles can be formed from an interpenetrating blend or composite of a plurality of materials where at least one material protrudes from the other materials at the surface of the particle after the removal of at least some of one or more materials. The particles have a plurality of pores that permit flow of a gas or a liquid through the particles. Each material is contiguous and the different materials form an interpenetrating structure. The particles are greater than 100 nm to about 10 μm in size and have protrusions that are small relative to the size of the particles such that a plurality of protrusions is present on a given particle. The particles have at least one hydrophobic material included in the plurality of materials, including the protruding material, or the particle is coated with a hydrophobic material such that the surface retains the general topography of protrusions from the surface of the particles and the surface is hydrophobic. The particles have pores, and a portion of these pores have connectivity through the particle by the removal of some or all of at least one of the non-protrusive (recessive) materials. The combination of a hydrophobic protruding material or hydrophobic coated surface with the topography of the particle results in super-hydrophobicity of the particles.

The hydrophobic material included in the particle or a coating on the particle can be any hydrophobic material. Preferably it is a perfluorinated or fluorinated organic material. The coating can be a fluorinated self-assembled monolayer.

There are no limits to the variations of sizes and shapes of the nanostructured surface. The blend or composite used to form the particles may be made from any materials differentially etchable by any known etching method or combination of methods. The materials comprising the particles can be any combination of glasses, metals, ceramics, and polymers.

The respective interpenetrating contiguous materials used to form the particles are differentially etchable (i.e. have different etch rates), when subjected to one or more etchants and have an interconnected structure with two or more phases, such as that resulting from spinodal decomposition. The phase separation permits the generation of a protrusive phase and a recessive phase by differentially etching the particles where one material phase is removed to a much greater degree than the other phase or phases. At one extreme, the entire more readily etched recessive phase can be removed entirely. Porosity results from the etching of the recessive phase to the extent that channels are formed within the particle, some of which may interconnect to form a continuous void generally, but not necessarily, with a tortuous path that extends from one side of the particle to another.

The protrusive material can have edges that are sharp or rounded depending upon the etching rate of the second (protrusive) material. For example, when the protrusive material can be etched at a significant rate and the recessive material can be etched at yet a higher rate, surface features result with sharp or tapered protrusive features as the proportion of the initial surface removed decreases with the depth of the etch leaving a peak or a ridge depending upon the shape of the protrusive material before etching. When the protrusive material undergoes very little or no etching the features can be blunter, more rounded rather than sharp.

The surface feature dimensions comprise width and length in the case of rectangular features, or diameter in the case of cylindrically shaped features that can be of any size smaller than the size of the entire particle. These features will generally have dimensions that are less than 1 μm and preferably have dimensions that are less than 400 nm. Generally, but not necessarily, the feature dimensions are of a relatively uniform distribution displaying a random pattern of shapes.

One method for producing the pre-etched composition starts with a plurality of materials that are more miscible at a first temperature but less miscible at a second temperature. For example, the mixture of materials can be miscible at a particular temperature and then separated into two or more phases when cooled or heat to a temperature where the materials are immiscible. Phase separation via spinodal decomposition, which results in two contiguous phases, is one available mechanism for formation of the contiguous interpenetrating materials. Nucleated decomposition is another mechanism for achieving such phase separated materials.

The particles can be prepared in any manner that results in a contiguous protruding phase with an optional interpenetrating contiguous recessive phase and the formation of the particles can occur prior to, subsequent to, or simultaneous with the surface features and pores. In one preferred embodiment, the composition of interpenetrating contiguous materials is formed and then partitioned into particles followed by differential etching of the materials to form the surface features and the pores. The partitioning of the composition of interpenetrating contiguous materials can be carried out by any means including pulverizing, chopping, or grinding the material. Other means can be used to form the particles and the particles can vary from uniform regular shapes to mixed irregular shapes. The particles can range from opaque to transparent. The particles can be separated using sieves or other methods as desired to achieve a desired particle size distribution.

The etching of at least one of the materials in the particles can be carried out before or after the formation of the particles. A preferred embodiment involves etching after the formation of the particle. In this manner the total surface area during etching is increased permitting more rapid etching than etching another form prior to partitioning into particles. Etching after partitioning into particles also permits the formation of particles where all facets of the particle have essentially the same kind of surface features. Where partitioning occurs after the etching, the relative depth between the protruding material and the recessing material can vary from one facet to another. The uniformity of the faceted surfaces can be preferred for some applications that use the particles of the invention and non-uniform facets can be preferred for other applications. Furthermore, the particles can be processed into a particular form such as an aggregate structure with particles optionally fixed with a binder prior to etching in the formation of a final article for use of the superhydrophobic particles.

The etching process can be of any known technique, such as contacting a fluid to preferentially remove one material over other materials. The fluid can be a liquid or a gas and can be diluted with a non-etchant. Plasma etching or other isotropic etch techniques can be employed. Mixtures of etchants can be used where all etchants are appropriate for the etching of a single material, some materials, or all materials in the composition, or where different etchants target specific materials within the composition. The product of the etchant with the materials of the composition of interpenetrating contiguous materials can be a gas, liquid or solid, and various means can be used to promote separation of the etch product from the freshly exposed portion of the interpenetrating contiguous materials. Etchants are those known to etch any material used to form the composition of interpenetrating contiguous materials. For example, aqueous hydrofluoric acid is an appropriate etchant for silica and many glasses and ceramics. Other acids and bases can be used as etchants for appropriate materials and even some solvents can be used as etchants with appropriate materials. The only requirement of the etchant or etchant mixture is that it can etch at least one of a mixture of interpenetrating contiguous materials at a greater rate than another material in the mixture such that the desired surface texture can be generated.

Once the desired particles with a desired particle size, particle shape, surface texture and pore content are generated, the particles can be rendered superhydrophobic. Superhydrophobic particles can result by coating the entire particle or the protruding material of the particle with a hydrophobic coating material. The coating is preferably a fluorinated material such as one that contains a perfuorinated alkyl or other organic moiety or any other highly hydrophobic materials. The coating material can be a self-assembled monolayer, a coupling agent, a sputtered material, or any other material that readily conforms to the surface and can be controlled such that the surface features formed upon etching are not filled or otherwise planerized during the coating process to an extent where superhydrophoicity is lost. The treatment of the particles with a coating material can be carried out after further processing the particles into a desired article. For example an aggregate of the particles can be formed with or without the aid of a binder prior to coating the particles to yield a stable superhydrophobic particulate surface.

Once the superhydrophobic particles are formed they can be used to generate a variety of articles, such as where they are used as discrete particles in a powder, as agglomerates, bound to each other, or bound to an additional substrate. The particles can be dispersed onto a surface to render that surface superhydrophobic. The superhydrophobic powder can be directly applied to many surfaces including wood products, textiles, bricks, cinder blocks, paper products, or any porous material. As indicated above, the steps of generating the superhydrophobic properties can be carried out after the attaching the particles to an article. These steps of rendering the particles superhydrophobic, including etching and coating, are optionally performed prior to or after combining the particles in some sort of array or aggregate but before combining with a substrate to form a desired article. The conversion of the particles into a useful form can include the addition of a binder to the particles. Furthermore, the binder can be any that chemically or physically locks the particles to each other or a substrate as long as the binder permits the maintenance or generation of the superhydrophobic surface. The use of a binder allows the application of the particles to nearly any surface including glasses, plastics, metals, and ceramics. Solvents and other processing aids can be included to the binder to facilitate binding and/or direct the binder to a desired portion of the particles and/or substrates. The use of such binders permits the formation of membranes, often with a porous substrate such as a woven fabric.

EXAMPLE

The present invention is further illustrated by the following specific Example, which should not be construed as limiting the scope or content of the invention in any way.

Figure 4:
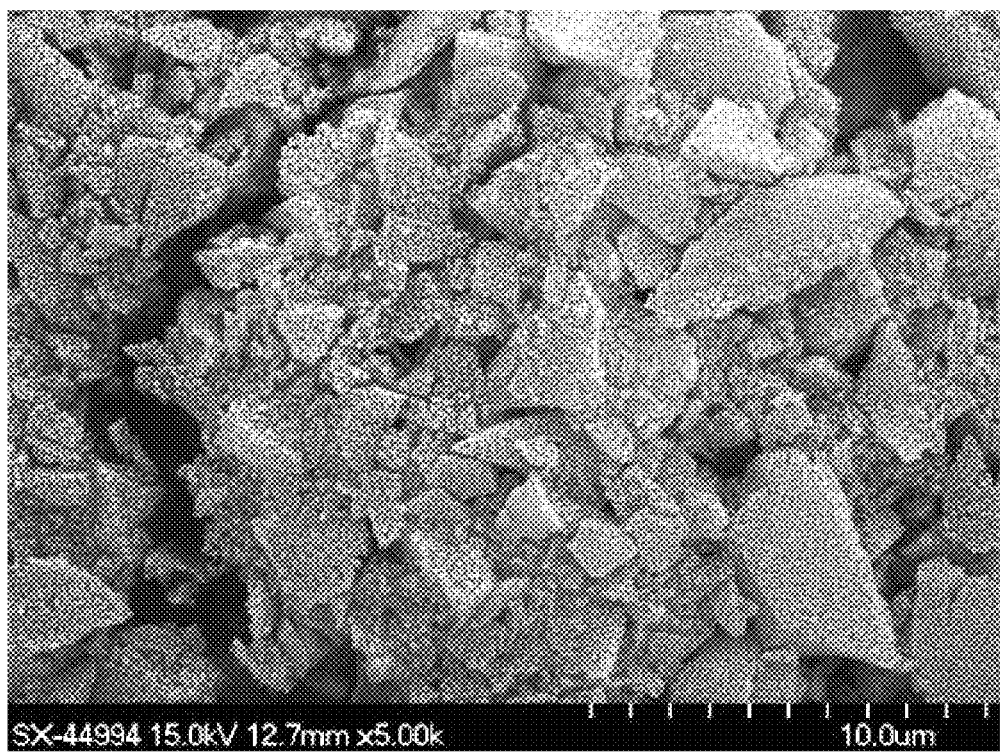
FIG. 4 is a scanning electron microscopy image (SEM) showing particles of an embodiment of the invention comprising irregularly shapes particles greater than about 0.2 μm to about 7 μm having protruding features that are about 200 nm in width and smaller.

A sample of EX24 glass (having a composition, in wt %, 65.9 $SiO_2$, 26.3 $B_2O_3$, and 7.8 $Na_2O$) having a thickness of 1 mm was heat treated for 20 min at 720° C. to induce phase separation. The glass was then ground to a powder. The powder was subsequently etched with 5% HF to produce a porous structure where essentially only a portion of the silica glass remained. The resulting glass powder was extremely hydrophilic. The powder was then converted from being hydrophilic to hydrophobic after drying by applying a hydrophobic self-assembled monolayer by immersing the powder in a solution of (tridecafluoro-1,1,2,2-tetrahydrooctyl)-trichlorosilane in hexanes and ultimately curing the monolayer by heating the powder at 110° C. for 15 minutes. A scanning electron microscope image of these particles is shown in FIG. 4 where all particles have a cross-section of more than about 0.5 μm to about 7 μm and protruding features of about 100 to 200 nm in width.

A hydrophilic powder, as prepared at the intermediate stage in the Example, can be suspended in water containing a bonding agent and applied to a substrate. The bound powder can then be converted to a superhydrophobic state by applying a hydrophobic self-assembled monolayer by contacting the powder coated substrate with (tridecafluoro-1,1,2,2-tetrahydrooctyl)-trichlorosilane, for example as a hexane solution, or other fluorinated bonding agent and ultimately curing the monolayer by heating the powder While there has been shown and described what are at present considered the preferred embodiments of the invention, it will be obvious to those skilled in the art that various changes and modifications can be prepared therein without departing from the scope of the inventions defined by the appended claims.

We claim:

1. A bandage comprising:
a substrate having
a top surface, and
a hydrophilic bottom surface opposed to the top surface;
a plurality of particles, ranging in size from about 100 nanometers to about 10 micrometers; and
a dressing attached to the hydrophilic bottom surface,
wherein the plurality of particles are formed from an interpenetrating blend having at least one protrusive phase,
wherein each of the plurality of particles has a plurality of spaced apart nanostructures defining an external boundary of each particle,
wherein a plurality of the spaced apart nanostructures are coated with a hydrophobic coating material that renders the plurality of particles superhydrophobic,
wherein each of the plurality of particles has a flow through porosity provided by a plurality of nanopores having connectivity through each particle,
wherein the plurality of particles are bound to the top surface with a binder,
wherein the substrate separates the superhydrophobic particles from the dressing,
wherein the binder does not diminish a topography of the spaced apart nanostructures, thereby allowing the plurality of particles to render the top surface superhydrophobic,
wherein the bandage has a water vapor transmission rate, measured according to ASTM Standard E96-80, of at least 50 $g/m^2/day$.

2. The bandage of claim 1, wherein the binder is selected from the group consisting of a polypropylene, a polystyrene, a polyacrylate, a cyanoacrylate, an amorphous fluoropolymer, an acrylic copolymer, an alkyd resin, and combinations thereof.

3. The bandage of claim 1, wherein the plurality of particles are bound to the top surface in a homogeneous distribution.

4. The bandage of claim 3, further comprising a dispersant, which facilitates the homogeneous distribution of the plurality of particles.

5. The bandage of claim 1, wherein the substrate is selected from the group consisting of a porous film, a perforated film, a textile, a nonwoven material, impregnated composites thereof, and combinations thereof.

6. The bandage of claim 1, wherein the bandage is selected from the group consisting of an adhesive bandage, a compression bandage, a wrap, a gauze, a medical tap, an orthopedic cast, and combinations thereof.

7. A method of making the bandage according to claim 1, comprising:
providing the substrate;
attaching the plurality of particles to the top surface of said substrate;
forming a plurality of superhydrophobic particles from the plurality of particles,
wherein said plurality of superhydrophobic particles comprise:
a protrusive material defining a plurality of nanopores and
a plurality of spaced apart nanostructures defining an external boundary of said hydrophobic particles,
wherein said nanopores provide a flow through porosity,
wherein said plurality of superhydrophobic particles range in size from about 100 nanometers to about 10 micrometers, wherein said first surface is hydrophobic after said method is complete; and attaching the dressing to the hydrophilic bottom surface of the substrate.

8. The method of claim 7, wherein said plurality of attached superhydrophobic particles render the top surface of said substrate superhydrophobic.

9. The method of claim 7, wherein the step of attaching the plurality of particles to the top surface of the substrate comprises:
forming a mixture comprising said plurality of particles and a solvent, and applying said mixture to said top surface.

10. The method of claim 9, wherein said solvent is volatile at a temperature of the applying step, and said top surface is soluble in said solvent.

11. The method of claim 7, wherein said attaching step comprises:
forming a mixture comprising said plurality of particles and a binder, and
applying said mixture to said top surface.

12. The method of claim 7, wherein the step of attaching the plurality of articles to the to surface of the substrate comprises:
applying said plurality of particles to said top surface while said top surface is adherent.

13. The method of claim 7, wherein said step of forming a plurality of superhydrophobic particles the plurality of particles occurs after said step of attaching the plurality of particles to the top surface of said substrate.

14. The method of claim 7, wherein said step of forming a plurality of superhydrophobic particles from the plurality of particles occurs before said step of attaching the plurality of particles to the top surface of said substrate.

15. The method of claim 7, wherein said substrate is breathable.

* * * * *